United States Patent [19]

Strini et al.

[11] 3,983,181

[45] Sept. 28, 1976

[54] PROCESS FOR THE CHLORINATION OF CHLORINATED ETHYLENE DERIVATIVES IN THE PRESENCE OF CHLORINATED ETHANE DERIVATIVES

[75] Inventors: Jean-Claude Strini; Yves Correia, both of Saint-Auban, France

[73] Assignee: Produits Chimiques Pechiney-Saint Gobain, Neuilly-sur-Seine, France

[22] Filed: Dec. 23, 1969

[21] Appl. No.: 887,777

[30] Foreign Application Priority Data
Dec. 27, 1968 France .............................. 68.181112

[52] U.S. Cl............................................. 260/658 R
[51] Int. Cl.²........................................ C07C 17/00
[58] Field of Search ................................ 260/658 R

[56] References Cited
UNITED STATES PATENTS
3,454,660   7/1969   Chuffart.......................... 260/658 R
3,475,504   10/1969   Kircher et al................... 260/658 R FOREIGN PATENTS OR APPLICATIONS
530,649    7/1931   Germany......................... 260/658 R
627,263    8/1949   United Kingdom............. 260/658 R
1,022,253  3/1966   United Kingdom............. 260/658 R OTHER PUBLICATIONS
Poutsma et al., JACS 86, pp. 3807–3814, (1964).

Primary Examiner—Delbert E. Gantz
Assistant Examiner—Joseph A. Boska

[57] ABSTRACT

A continuous process for the chlorination of one or more dichlorinated ethylene derivatives and/or vinyl chloride in admixture with one or more chlorinated ethane derivatives, said reaction being carried out in a liquid phase in the absence of catalyst and in the absence of light radiations by passing the mixture with molecular chlorine through at least two reaction zones in series at a temperature within the range of 20°–90° C.

9 Claims, No Drawings

PROCESS FOR THE CHLORINATION OF CHLORINATED ETHYLENE DERIVATIVES IN THE PRESENCE OF CHLORINATED ETHANE DERIVATIVES

This invention relates to a liquid phase chlorination in the absence of catalyst and in the absence of light radiations of one or more chlorinated ethylene derivatives in the presence of chlorinated ethane derivatives.

It is known that chlorination of 1,1-dichloroethylene, in the presence of light, with or without ferric chloride, as catalyst, yields 1,1,1,2-tetrachloroethane. According to applications Ser. No. 786,736, filed Dec. 24, 1968, and Ser. No. 786,740, filed Dec. 24, 1968, it is also known that 1,1-dichloroethylene and/or cis- and/or trans-1,2-dichloroethylenes, in the absence of light and catalyst, yield respectively 1,1,1,2-tetrachloroethane and/or 1,1,2,2-tetrachloroethane.

However, when it is sought continuously to chlorinate, in a single homogeneous reaction zone, ethylene chlorinated derivatives, such as 1,1-dichloroethylene and/or cis- and trans-1,2-dichloroethylenes, in the presence of chlorinated ethane derivatives, such as ethyl chloride and 1,1-dichloroethane, it has been observed that significant amounts of substitution products of the order of 50 molar % and more, based upon the involved amount of said chlorinated ethane derivatives, are obtained. This occurs more particularly when it is desirable to convert almost quantitatively one or more chlorinated ethylene derivatives into chlorinated ethane derivatives.

Our search has led to the discovery that the amount of substitution products of one or more of the chlorinated ethane derivatives initially present in the mixture to be chlorinated depends on the conversion rate which is desired to be obtained of the chlorinated ethylene derivatives present in the mixture to be chlorinated and that the use of a system composed of a series of homogeneous reaction zones permits conversion rates higher than those obtained in a single reaction zone for a defined substitution rate of said chlorinated ethane derivatives to be obtained or to diminish considerably the substitution rate for a defined conversion rate of said ethylene derivatives. In this specification, the term "substitution rate" is used to define the ratio: moles of chlorine having been fixed by substitution of one or more chlorinated ethane derivatives / total moles of chlorine having reacted on the chlorinated ethane derivatives as well as on the chlorinated ethylene derivatives.

We have also found that the volume of each of the reaction zones is solely a function of the conversion rate of said chlorinated ethylene derivatives which is desired to be obtained in each of the reaction zones.

In accordance with the practice of this invention, one or several dichlorinated ethylene derivatives and/or vinyl chloride, in admixture with one or several chlorinated ethane derivatives, are reacted continuously in the liquid phase with molecular chlorine in at least two reaction zones arranged in series, in the absence of light radiation and at a temperature within the range of 20°–90° C and preferably within the range of 50°–70° C and in the absence of catalyst.

The term "absence of catalyst" means that traces of Fe, Ni, Al, Cu, Ti, Sb, S and/or P may be present in the reaction medium, more particularly in the form of a chloride, either as impurities or as a result of corrosion of the process plant material. However, such trace amounts in either of the reaction zones should be less than 0.004% by weight, expressed in the form of chloride and based upon the reaction liquid phase, and preferably less than 0.0025% by weight.

According to this invention, molecular chlorine is introduced into the reaction medium so as to provide an amount of chlorine dissolved in each of the reaction zones within the range of 0.5 to 20 grams per liter and preferably within the range of 2 to 7 grams per liter. However, it should be noted that the amount of chlorine to be introduced depends not only on the desired conversion rate of the chlorinated ethylene derivatives but varies also with the feed composition submitted to chlorination, since the substitution rate of each of the chlorinated ethane derivatives differs from one chlorinated ethane compound to another.

The chlorinated ethane derivatives in admixture with one or more dichlorinated ethylene derivatives and/or vinyl chloride can represent from 1 to 80 molar % and preferably at least 10 molar % based on said mixture to be chlorinated. The chlorinated ethane derivatives are more particularly composed of: ethyl chloride (0 to 60 molar %); 1,1-dichloroethane (0 to 80 molar %); 1,2-dichloroethane (0 to 60 molar %); 1,1,1-trichloroethane (0 to 60 molar %); 1,1,2-trichloroethane (0 to 80 molar %); 1,1,1,2-tetrachloroethane (0 to 80 molar %); 1,1,2,2-tetrachloroethane (0 to 80 molar %); and pentachloroethane (0 to 40 molar %).

Under the operating conditions of this process, only a part of the chlorinated ethane derivatives of the initial mixture undergoes substitution by chlorine. Thus, ethyl chloride is converted partially into 1,1-dichloroethane and into 1,2-dichloroethane in a ratio 1,1-dichloroethane / 1,2-dichloroethane varying between 1.6 and 1.8; 1,2-dichloroethane is converted into 1,1,2-trichloroethane, 1,1-dichloroethane into 1,1,1-trichloroethane and 1,1,2-trichloroethane in a ratio 1,1,1-trichloroethane / 1,1,2-trichloroethane varying between 1.9 and 2.1; 1,1,2-trichloroethane is converted into 1,1,2,2-tetrachloroethane and 1,1,1,2-tetrachloroethane in a ratio 1,1,2,2-tetrachloroethane / 1,1,1,2-tetrachloroethane of about 1; 1,1,2,2-tetrachloroethane and 1,1,1,2-tetrachloroethane are converted into pentachloroethane, and pentachloroethane is converted into hexachloroethane.

The chlorinated ethylene derivatives of the initial mixture are converted under the operating conditions of the process, and according to the conversion rate desired into addition chlorination derivatives. Thus vinyl chloride yields 1,1,2-trichloroethane; cis- and trans-dichloroethylene yield symmetrical tetrachloroethane and 1,1-dichloroethylene yields unsymmetrical tetrachloroethane.

The chlorination reaction can be carried out in a solvent medium on the condition that the solvent is inert to molecular chlorine under the operating conditions of the invention. For this purpose, use can be made of such solvents as carbon tetrachloride and pentachlorofluoroethane.

According to a practical embodiment of this invention, it is sufficient to limit the number of reaction zones to a number which does not exceed four and it is desirable to achieve a conversion of chlorinated ethylene derivatives at about the same rate in each of the reaction zones, thereby to enable use of reaction zones of substantially equal volume. The total residence time of the reactants in each of the reaction zones depends on the conversion rate desired to be obtained of the chlorinated ethylene derivatives subjected to chlorination. For example, for conversion rates ranging from 80 to 99.5 molar %, the total residence time will be between 2 and 9 hours. The term "residence time" is intended to refer to the ratio between the volume of the particular reaction zone to the volume per hour of effluent which flows from said reaction zone.

The molecular chlorine used in the practice of this invention can be either in the form of liquid chlorine, which is gasified before reaction, or in the form of chlorine gas, such as is collected at the exit of plants producing chlorine by electrolysis of an aqueous solution of sodium chloride. In this connection, applicants have noticed that the yield in addition product of chlorinated ethylene derivatives is practically unmodified, whether use is made of a 99.9% pure liquid chlorine or a commercial 95% pure chlorine, in which the main impurities are $CO_2$, $O_2$, $N_2$, $H_2$ and $CO$. The chlorine used can be diluted with gases which do not react under the reaction conditions, such for example as hydrochloric acid and the gases which have been stated above. A chlorine dilution by inert gases in molecular ratio up to 1:1 is not detrimental to the reaction but it is generally undesirable to have to handle large volumes of inert gases since the productivity of the process will naturally be decreased while the chlorine losses will be increased by entrainment with inert gases.

According to this invention, the chlorinated ethylene derivatives which are desired to be chlorinated should be free or practically free (below 0.001% by weight) of stabilizers which often are incorporated, such as phenol or p-methoxyphenol. These should be eliminated before carrying out the described chlorination reaction.

The process of this invention permits considerable increase in the conversion rate of chlorinated ethylene derivatives for a given substitution rate of the chlorinated ethane derivatives by comparison with the process employing only a single reaction zone. Inversely, for a given conversion rate of chlorinated ethylene derivatives, the process of this invention makes it possible to decrease the rate of the substitution products of chlorinated ethane derivatives initially present in admixture with chlorinated ethylene derivatives.

The use of positive pressure, in the order of a few bars and preferably from 1 to 2 bars, makes it possible to increase the kinetics of the chlorination reaction by increasing the amount of chlorine dissolved in the reaction medium but does not interfere in the increase or decrease of the substitution rate of the chlorinated ethane derivatives in the mixture to be chlorinated. However, such positive pressure is not always advantageous in that it has a tendency to increase the chlorine losses.

According to this invention, the effluent of the last chlorination reaction zone generally contains various chlorinated derivatives of aliphatic hydrocarbons and molecular chlorine which is dissolved therein. The dissolved chlorine in the effluent can be eliminated either by heating up to 90° C and preferably between 40° and 70° C and/or entrainment by means of an inert gas flow with respect to the effluent, such as nitrogen or air, or by conversion into 1,2-dichloroethane by passing in contact with an adequate amount of gaseous ethylene; the isolation of each of the chlorinated derivatives of aliphatic hydrocarbons is carried out by distillation.

The following examples are given by way of illustration, but not by way of limitation, of said invention.

EXAMPLE 1

Into a first reaction zone composed of a nickel reactor, there are introduced continuously at 60° C, 100 moles/hour of a mixture composed of: 50 molar % of 1,1-dichloroethylene, 25 molar % of 1,1-dichloroethane, 15 molar % of 1,2-dichloroethane and 10 molar % of ethyl chloride. A previously gasified stream of liquid chlorine is allowed to pass continuously into said reactor at a rate to maintain a dissolved chlorine content in said mixture within the range of 3 to 5 grams per liter of reaction medium. The residence time of the reactants in this reactor is about 3 hours. The liquid effluent of the first reaction zone is introduced into a second reaction zone composed of a nickel reactor having a volume equal to the first. A previously gasified liquid chlorine flow is passed into this second reactor in an amount to give a dissolved chlorine content within the range of 3 to 5 grams per liter. The reaction medium temperature is 60° C and the residence time of the reactants is about 3 hours. The dissolved chlorine, which is unreacted, is recovered by air stripping of the second reactor effluent.

The following table summarizes the results obtained:

|  | Molar composition of the initial mixture | Molar composition of the second reactor effluent |
|---|---|---|
| 1,1-dichloroethane | 25 | 25.7 |
| 1,2-dichloroethane | 15 | 12 |
| 1,1-dichloroethylene | 50 | 1 |
| ethyl chloride | 10 | 4.8 |
| 1,1,1,2-tetrachloroethane |  | 48.2 |
| 1,1,2-trichloroethane |  | 5.6 |
| 1,1,1-trichloroethane |  | 1.6 |
| 1,1,2,2-tetrachloroethane |  | 0.3 |
| pentachloroethane and hexachloroethane |  | 0.2 |
| chlorinated derivatives heavier than the preceding |  | 0.6 |

The mixture of compounds is separated by distillation. The conversion rate of 1,1-dichloroethylene is 99%. The substitution rate, as defined in this specification, of the initial chlorinated ethane derivatives is about 22.8 molar %.

By way of comparison, chlorination of the initial mixture of Example 1 has been carried out but in a single reaction zone composed of a single nickel reactor having a volume such that the residence time in this reactor is about 6 hours. All other operating conditions remain the same as in Example 1.

The results obtained are summarized in the following table:

|  | Molar composition of the initial mixture | Molar composition of the reaction zone effluent |
|---|---|---|
| 1,1-dichloroethane | 25 | 25.6 |
| 1,2-dichloroethane | 15 | 12.4 |
| 1,1-dichloroethylene | 50 | 4.4 |
| ethyl chloride | 10 | 5.6 |
| 1,1,1,2-tetrachloroethane |  | 44.3 |
| 1,1,2-trichloroethane |  | 4.8 |
| 1,1,1-trichloroethane |  | 1.4 |
| 1,1,2,2-tetrachloroethane |  | 0.1 |
| pentachloroethane and hexachloroethane |  | 0.8 |
| chlorinated derivatives heavier than the preceding |  | 0.6 |

For a same substitution rate as that obtained in Example 1, there is observed a conversion rate of 1,1-dichloroethylene of only 95.6%.

In another comparative test, there has been also operated in a single reaction zone, but by advancing chlorination to reach a conversion rate of 1,1-dichloroethylene to a value of 99% as in Example 1. It is found that the substitution rate, as defined in the above specification, reaches 39.6%, thus showing that chlorination of the initial chlorinated ethylene derivatives in a single reaction zone is less selective than that carried out in two reaction zones arranged in series.

The reaction zone effluent has the following molar composition:

| 1,1-dichlroethane | 22.9 |
|---|---|
| 1,2-dichloroethane | 8.3 |
| 1,1-dichloroethylene | 1.0 |
| ethyl chloride | 2.8 |
| 1,1,1,2-tetrachloroethane | 46.2 |
| 1,1,2-trichloroethane | 10.2 |
| 1,1,1-trichloroethane | 4.4 |
| 1,1,2,2-tegrachloroethane | 0.8 |
| pentachloroethane and hexachloroethane | 2.8 |
| chlorinated derivatives heavier than the preceding | 0.6 |

EXAMPLE 2

Into a first reaction zone composed of a nickel reactor, there are introduced continuously at 60° C, 100 moles/hour of a mixture having the following molar composition:

| 1,1-dichloroethane | 20 |
|---|---|
| 1,2-dichloroethane | 20 |
| 1,1,2-trichloroethane | 10 |
| trans-1,2-dichloroethylene | 20 |
| cis-1,2-dichloroethylene | 30 |

A previously gasified liquid chlorine flow is allowed to pass continuously into said reactor in amounts to provide a dissolved chlorine content in said mixture comprised between 3 and 5 grams per liter. The residence time of the reactants in this reactor is about 2.5 hours. The first reaction zone liquid effluent is introduced into a second reaction zone composed of a reactor identical to the first reactor. A previously gasified liquid chlorine flow is allowed to pass continuously and simultaneously into this second reactor so as to maintain a dissolved chlorine content of between 3 and 5 grams per liter. The reaction medium temperature is 60° C and the residence time of the reactants is about 2.5 hours.

The following table summarizes the results observed:

|  | Molar composition of the initial mixture | Molar composition of the second reactor effluent |
|---|---|---|
| 1,1-dichloroethane | 20 | 18.3 |
| 1,2-dichloroethane | 20 | 14.4 |
| 1,1,2-trichloroethane | 10 | 15.6 |
| cis-1,2-dichloroethylene | 30 | 0.8 |
| trans-1,2-dichloroethylene | 20 | 0.6 |
| 1,1,1-trichloroethane |  | 1.1 |
| 1,1,1-2-tetrachloroethane |  | 0.2 |
| 1,1,2,2-tetrachloroethane |  | 47.6 |
| pentachloroethane and hexachloroethane |  | 0.8 |
| chlorinated derivatives heavier than the preceding |  | 0.6 |

The second reactor effluent is treated by an ethylene flow in order to recover the molecular chlorine dissolved therein (from 3 to 5 g/l), in the form of 1,2-dichloroethane. The mixture constituents are then separated by distillation. The conversion rate of the cis- and trans-1,2-dichloroethylenes is 97.6% and the substitution rate as defined above in the specification is 19.1%.

By way of comparison, chlorination of the initial mixture of Example 2 has been carried out but in a single reaction zone composed of a single nickel reactor having a volume such that the residence time in this reactor is about 5 hours. All other operating conditions remain unmodified with regard to the ones of Example 2.

The reaction zone effluent has the following molar composition:

| | |
|---|---|
| 1,1-dichloroethane | 16.2 |
| 1,2-dichloroethane | 10.6 |
| 1,1,2-trichloroethane | 18.7 |
| 1,1,1-trichloroethane | 2.5 |
| cis-1,2-dichloroethylene | 0.8 |
| trans-1,2-dichloroethylene | 0.6 |
| 1,1,1,2-tetrachloroethane | 0.8 |
| 1,1,2,2-tetrachloroethane | 46.9 |
| pentachloroethane and hexachloroethane | 2.3 |
| chlorinated derivatives heavier than the preceding | 0.6 |

For a same conversion rate of cis- and trans-1,2-dichloroethylenes as that obtained in Example 2, it is noticed that the substitution rate of the initial chlorinated ethane derivatives increased up to 26.8%.

EXAMPLE 3

The operation is the same as in Example 2, but with the following characteristics and under the following operating conditions:

1st reactor
Centesimal molar composition of the mixture introduced:
| | |
|---|---|
| 1,1,2-trichloroethane | 10 |
| 1,2-dichloroethane | 20 |
| 1,1-dichloroethane | 5 |
| ethyl chloride | 5 |
| 1,1-dichloroethylene | 30 |
| cis-1,2-dichloroethylene | 20 |
| trans-1,2-dichloroethylene | 10 | temperature : 60° C
dissolved chlorine content in said composition: 6 to 7 g/l
residence time of the reactants : 4 hours.

2nd reactor
temperature : 60° C
dissolved chlorine content in the reaction medium: 6 to 7 g/l
centesimal molar composition of the effluent:
| | |
|---|---|
| 1,1,1-trichloroethane | 1.0 |
| 1,2-dichloroethane | 9.6 |
| 1,1-dichloroethane | 5.9 |
| 1,1,2-trichloroethane | 20.2 |
| 1,1,1,2-tetrachloroethane | 29.2 |
| 1,1,2,2-tetrachloroethane | 29.3 |
| pentachloroethane and hexachloroethane | 3.1 |
| ethyl chloride | 1.1 |
| 1,1-dichloroethylene | 0.1 |
| cis-1,2-dichloroethylene | 0.1 |
| trans-1,2-dichloroethylene | 0.1 |
| chlorinated derivatives heavier than the preceding | 0.3 |

The second reactor effluent is treated as in Example 2 in order to convert the chlorine which is dissolved therein. The various constituents are then separated by distillation. The conversion rate of the dichlorinated ethylene derivatives is 99.5% and the substitution rate as defined above in the specification of the chlorinated ethane derivatives is 28.9%.

By way of comparison, a chlorination as in Example 3 has been carried out, except that it has been operated in a single reactor, the volume of which is such that the residence time in this reactor is about 8 hours. All other operating conditions remain unmodified with regard to those of Example 3. The reaction zone effluent has the following centesimal molar composition:

| | |
|---|---|
| 1,1,1-trichloroethane | 2.5 |
| 1,2-dichloroethane | 4.6 |
| 1,1-dichloroethane | 4.0 |
| 1,1,2-trichloroethane | 19.6 |
| 1,1,1,2-tetrachloroethane | 28.5 |
| 1,1,2,2-tetrachloroethane | 28.4 |
| pentachloroethane and hexachloroethane | 11.3 |
| ethyl chloride | 0.5 |
| 1,1-dichloroethylene | 0.1 |
| cis-1,2-dichloroethylene | 0.1 |
| trans-1,2-dichloroethylene | 0.1 |
| chlorinated derivatives heavier than the preceding | 0.3 |

For the same conversion rate of the dichlorinated ethylene derivatives as that obtained in Example 3, the substitution rate of the initial chlorinated ethane derivatives increased up to 46%.

EXAMPLE 4

The method according to Example 3 is operated, but under the following operative conditions:

1st reactor
Centesimal molar composition of the mixture introduced:
| | |
|---|---|
| vinyl chloride | 10 |
| 1,1-dichloroethylene | 20 |
| trans-1,-2dichloroethylene | 10 |
| cis-1,2-dichloroethylene | 10 |
| 1,1-dichloroethane | 15 |
| 1,2-dichloroethane | 20 |
| ethyl chloride | 5 |
| 1,1,1-trichloroethane | 5 |
| 1,1,2-trichloroethane | 5 |

Introduction of molecular chlorine to maintain a dissolved chlorine content of 5 to 7 g/l
Temperature : 60° C
Residence time of the reactants : 4 hours 2nd reactor
temperature : 60°C
introduction of molecular chlorine to maintain a dissolved chlorine content of 5 to 7 g/l
residence time of the reactants : 4 hours
centesimal molar composition of the effluent :
| | |
|---|---|
| vinyl chloride | 0.05 |
| 1,1-dichloroethylene | 0.1 |
| trans-1,2-dichloroethylene | 0.05 |
| cis-1,2-dichloroethylene | 0.05 |
| ethyl chloride | 1.05 |
| 1,1-dichloroethane | 13.8 |
| 1,2-dichloroethane | 9.7 |
| 1,1,1-trichloroethane | 7.4 |
| 1,1,2-trichlroethane | 25.2 |
| 1,1,2,2-trichloroethane | 20.3 |
| 1,1,1,2-tetrachloroethane | 19.9 |

| | |
|---|---|
| pentachloroethane and hexachloroethane | 2.0 |
| chlorinated derivatives heavier than the preceding | 0.4 |

The second reactor effluent has been treated in the same manner as in Example 3 in order to convert the chlorine which is dissolved therein. It has then been processed for the separation of the various constituents by distillation.

The conversion rate of mono- and dichlorinated ethylene derivatives is 99.5% and the substitution rate, as defined above in the specification, of the chlorinated ethane derivatives is 33.1%.

By way of comparison, a chlorination like that in Example 4 has been carried out, except that it has been operated with a single reactor, the volume of which is such that the residence time in said reactor is about 8 hours. All other operating conditions remain unmodified. The reaction zone effluent has the following centesimal molar composition:

| | |
|---|---|
| vinyl chloride | 0.05 |
| 1,1-dichloroethylene | 0.10 |
| trans-1,2-dichloroethylene | 0.05 |
| cis-1,2-dichloroethylene | 0.05 |
| ethyl chloride | 0.75 |
| 1,1-dichloroethane | 10.8 |
| 1,2-dichloroethane | 6.25 |
| 1,1,1-trichloroethane | 9.55 |
| 1,1,2-trichloroethane | 25.1 |
| 1,1,2,2-tetrachloroethane | 20.95 |
| 1,1,1,2-tetrachloroethane | 20.5 |
| pentachloroethane and hexachloroethane | 5.45 |
| chlorinated derivatives heavier than the preceding | 0.40 |

For a same conversion rate of mono- and -dichlorinated ethylene derivatives as that obtained in Example 4, it is noticed that the substitution rate of the initial chlorinated ethane derivatives represents a net increase: it passed from 33.1% to 44.7%.

While the specification makes use of the term "chlorinated ethylene derivatives," it will be understood that the term will include "chlorinated ethylene derivative" when but a single derivative is employed.

It will be further understood that changes may be made in the details of formulation and operation without departing from the spirit of the invention, especially as defined in the following claims.

We claim:

1. A continuous process for chlorination of one or more dichloroethylenes and/or vinyl chloride in admixture with 1 to 80 mole% of one or more chloroethanes containing 1 to 5 chlorine atoms based on the total of the dichloroethylenes and/or vinyl chloride and the chloroethanes in liquid phase comprising passing the mixture with molecular chlorine through at least two homogeneous reaction zones in series at a temperature within the range of 20°–90°C in the absence of catalyst and in the absence of light radiations, wherein the molecular chlorine is present in an amount in each reaction zone to provide chlorine dissolved in the reaction medium within the range of 0.5 to 20 grams per liter.

2. A process as claimed in claim 1 in which the molecular chlorine is introduced in each of said reaction zones in an amount to provide chlorine dissolved in the reaction medium within the range of 2 to 7 grams per liter.

3. A process as claimed in claim 1 in which the number of reaction zones is no greater than four.

4. A process as claimed in claim 1 in which the reaction zones are of substantially equal volume.

5. A process as claimed in claim 1 in which the reactants are present in the reaction zone for a total residence time within the range of 2 to 9 hours.

6. A process as claimed in claim 1 in which the chlorinated ethylene derivatives subjected to chlorination reaction contain less than 0.001% by weight stabilizer.

7. A process as claimed in claim 1 in which Fe, Ni, Al, Cu, Ti, Sb, S and P are present in each of the reaction zones in amounts less than 0.004% by weight, expressed as the corresponding chloride when based upon the reaction liquid phase.

8. A process as claimed in claim 1 in which the reaction pressure is from 1 to 2 bars.

9. A process as claimed in claim 1 in which the chlorination reaction is carried out in a solvent medium in which the solvent is inert to molecular chlorine.

* * * * *